United States Patent [19]

Islava

[11] Patent Number: 5,402,776
[45] Date of Patent: Apr. 4, 1995

[54] ENDOTRACHEAL TUBE HOLDER

[76] Inventor: Steven T. Islava, 534 Catalina Dr., Newport Beach, Calif. 92663

[21] Appl. No.: 234,540

[22] Filed: Apr. 28, 1994

[51] Int. Cl.$^6$ ..................... A61M 25/01; A61M 31/00
[52] U.S. Cl. ......................... 128/207.17; 128/207.14; 128/911; 128/DIG. 26; 604/174; 604/178; 604/250
[58] Field of Search ................. 128/207.17, DIG. 26, 128/911, 912, 207.14, 200.24, 200.26; 604/174, 177, 178, 179, 250

[56] References Cited

U.S. PATENT DOCUMENTS

| | | | |
|---|---|---|---|
| 2,908,269 | 10/1959 | Cheng | 128/DIG. 26 |
| 4,249,529 | 2/1981 | Nestor et al. | 128/207.17 |
| 4,331,143 | 1/1982 | Kemiya | 128/305.15 |
| 4,351,331 | 9/1982 | Gereg | 128/207.14 |
| 4,449,527 | 5/1984 | Hinton | 128/207.17 |
| 4,537,192 | 8/1985 | Foster | 128/207.17 |
| 4,683,882 | 8/1987 | Laird | 128/207.17 |
| 4,744,358 | 5/1988 | McGinnis | 128/207.17 |
| 4,832,019 | 5/1989 | Weinstein et al. | 128/207.17 |
| 4,867,154 | 9/1989 | Potter et al. | 128/207.17 |
| 5,009,227 | 4/1991 | Nieuwstad | 128/207.17 |
| 5,097,827 | 3/1992 | Izumi | 128/DIG. 26 |
| 5,105,807 | 4/1992 | Kahn et al. | 128/912 |

Primary Examiner—Edgar S. Burr
Assistant Examiner—William J. Deane, Jr.
Attorney, Agent, or Firm—Harold L. Jackson

[57] ABSTRACT

An endotracheal tube holder that includes a face plate assembly which is attached to a patient's head by an adjustable headband. The face plate assembly is formed with a face plate adapted to be positioned over the mouth of the patient and is formed with an open end channel terminating with a V-shaped notch over which is superposed a tube holding block that is affixed to the outer surface of the face plate, and also includes a matching V-shaped notch in which an endotracheal tube can be fixedly positioned by a thumb screw, a bite block being integrally secured to the inner surface of the face plate which is also provided with an aligned V-shaped notch. The face plate also includes an opening for ready access to the patient's mouth, as might be required.

25 Claims, 2 Drawing Sheets

ENDOTRACHEAL TUBE HOLDER

BACKGROUND OF THE INVENTION

1. Field of the Invention

The present invention relates generally to an endotracheal tube apparatus and more particularly to an endotracheal tube holder having an improved V-shaped tube securing device whereby the endotracheal tube is held in a positive secured manner within the tube holder after the tube is inserted in the patient's trachea so that the endotracheal tube is fixedly mounted to prevent inadvertent movement after the tube has been properly positioned within the trachea.

2. Description of the Prior Art

Endotracheal tube devices are used under several conditions such as for ventilating a patient during anesthesia, for resuscitation, as well as during critical care not only in the hospital but also during the time when a patient is being transported.

It is well known in the art that various problems and difficulties are being encountered in providing suitable means for securing an endotracheal tube in a simple and positive manner to the tube-holding device which is part of the mouthpiece of the face plate assembly.

Many types of securing arrangements have been tried in the prior art which very often included simply mounting the tube in place with adhesive tape to several areas of the patient's face.

Some endotracheal tubes were mounted in a face plate that included a bite block whereby the patient was required to grip the bite block with his or her teeth. However, other prior art tube holders have included locking means for securing the endotracheal tube to the face plate of the tube holder.

For typical examples of prior art endotracheal tube holders one may refer to those disclosed in the following U.S. Pat. Nos.:

4,867,154 issued to A. Potter, et. al.;
4,832,019 issued to B. Weinstein;
4,744,358 issued to G. McGinnis;
4,537,192 issued to B. Foster;
4,449,527 issued to D. Hinton;
4,249,529 issued to J. Nestor, et. al.

BRIEF SUMMARY AND OBJECTS OF THE INVENTION

The present invention defines an endotracheal tube holder formed with a face plate adapted to fit over the patient's mouth area below the nose and just above the chin with the extending longitudinal sides being arranged to cover the patient's lip area.

An adjustable head strap is attached to slotted openings positioned adjacent the outer free edges of the face plate to allow adjustment from either side.

The face plate has an inverted, substantially L-shaped channel having an open end to receive an endotracheal tube which is positioned in an inwardly extended V-shaped portion of the channel.

A mouthpiece that defines a bite block is fixedly mounted to the inner facing side of the face plate. The bite block is also provided with a V-shaped notch to correspond to the V-shaped portion of the channel.

On the outer side of the face plate is a positive tube securing means defined by a tube holding block assembly having a L-shaped channel and V-shaped recess corresponding to the face plate, whereby the endotracheal tube can be first positioned in the patient's mouth and throat prior to mounting the tube holder. After the tube holder is positioned over the endotracheal tube, a suitable thumb screw is mounted to one side of the tube-holding block assembly and is then adjustably engaged with the tube, thereby forcing the tube to become fixedly wedged in a locked position in the "V" portion that is defined by the holding block assembly.

Thus, the present invention has for an important object a provision wherein the face plate of the endotracheal tube holder includes a positive holding means for the endotracheal tube that comprises an integral tube-holding block assembly formed with a tube receiving channel, the closed end of the channel being defined by a V-shaped notch in which the tube is fixedly engaged by means of an adjustable thumb screw. This novel tube-holding block assembly prevents the endotracheal tube from moving in a longitudinal direction and also inhibits rotational movement once the tube is properly positioned in the patient's trachea.

Another object of the present invention is to provide an endotracheal tube holder that will accommodate a number of different sizes of tubes and lock the selected tube firmly in place.

Still another object of the invention is to provide an endotracheal tube holder with an integral bite block having a corresponding V-shaped notch to receive the tube therethrough so that the bite block further aids in the alignment of the tube within the mouth of the patient.

A further object of the present invention is to provide an endotracheal tube holder wherein the face plate includes an aperture which allows additional access to the interior of the patient's mouth without interfering with the position of the endotracheal tube.

Still another object of the present invention is to provide a tube holder of this character that includes an adjustable headband arranged to be adjustably attached to the opposite ends of the face plate by VELCRO ® or other suitable securing material.

A still further object of the invention is to provide a tube holder of this character that is simple in construction and relatively inexpensive to manufacture.

The characteristics and advantages of the invention are further sufficiently referred to in connection with the accompanying drawings, which represent one embodiment.

After considering this example, skilled persons will understand that variations may be made without departing from the principles disclosed; and I contemplate the employment of any structures, arrangements or modes of operation that are properly within the scope of the appended claims.

BRIEF DESCRIPTION OF THE DRAWINGS

With the above and related objects in view, the invention consists in the details of construction and combination of parts, as will be more fully understood from the following description, when read in conjunction with the accompanying drawings and numbered parts.

DETAILED DESCRIPTION OF THE INVENTION

Figure 1:
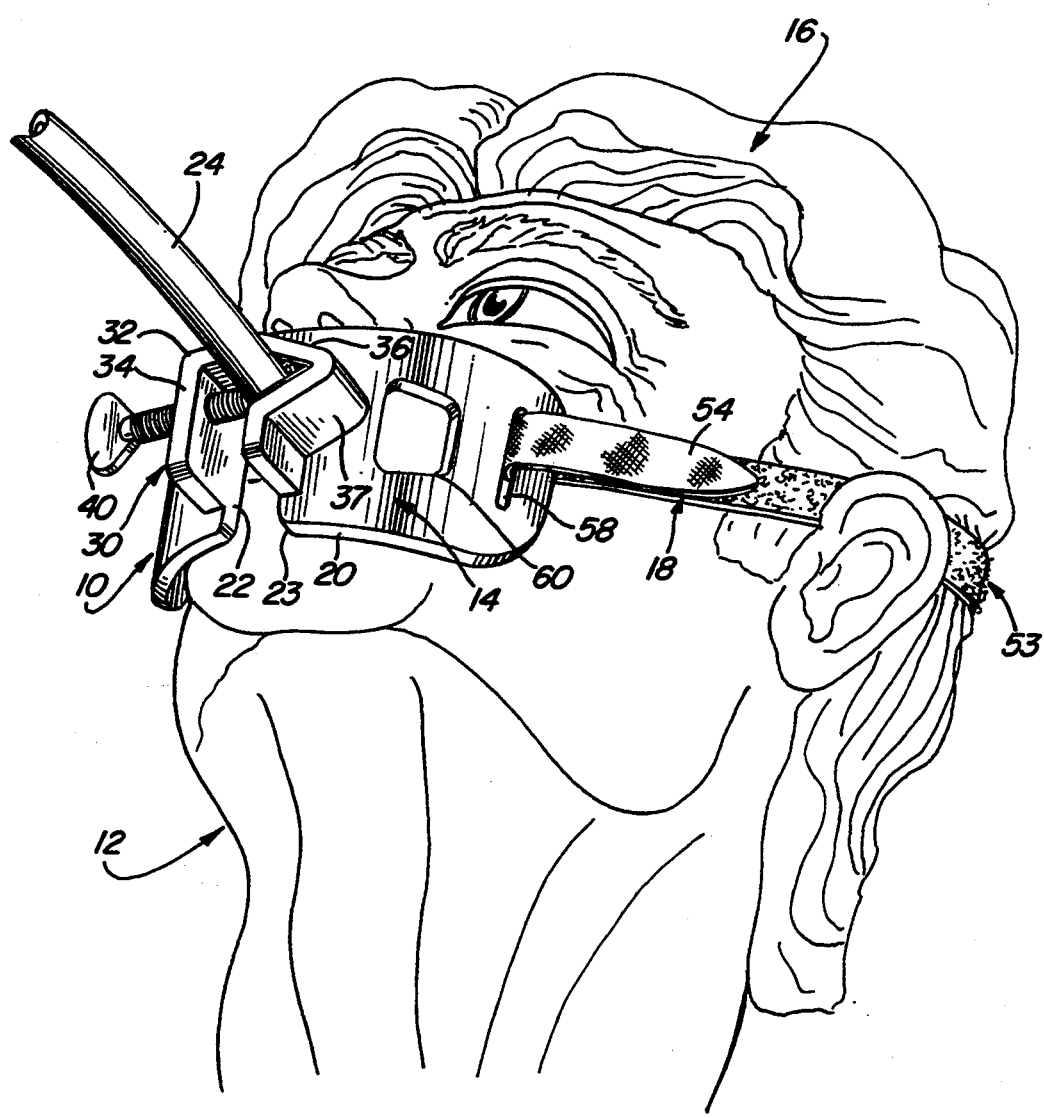
FIG. 1 is a pictorial view of an endotracheal tube holder of the present invention mounted in an operating position as worn by a patient.

Referring more particularly to FIG. 1, there is shown the preferred embodiment of the present invention which is defined as an endotracheal tube-holder apparatus, generally indicated at 10, and illustrated as it would be typically worn by a patient 12.

The endotracheal tube-holder apparatus 10 is defined by a face-plate assembly, indicated generally at 14, which is securely mounted to the patient's head 16 by means of an adjustable attaching means 18, and will be hereinafter described in more detail. Face-plate assembly 14 comprises an elongated arcuate face plate 20 made of a suitable thermoplastic material adapted to be positioned over a patient's face so as to directly cover the mouth by means of the adjustable attaching means 18. The material from which the face place member is made should be sufficiently flexible to fit the contour of the patient's face.

Face-plate member 20 is formed with a channel 22 which has a substantially inverted L-shape configuration, the channel having an open end 23 to receive an endotracheal tube 24 and a closed end 26 in which tube 24 is fixedly secured.

The endotracheal tube is generally positioned within the patient's mouth so as to be properly inserted within the trachea. Once the endotracheal tube 24 is properly positioned therein it should not be allowed to move longitudinally or to rotate. This is readily accomplished by mounting face-plate assembly 14 over endotracheal tube 24 by positioning the open end 23 of channel 22 to receive tube 24, whereby the tube 24 is further positioned within closed end 25 of the channel which is formed as a substantially V-shaped notch 26.

Figure 2:
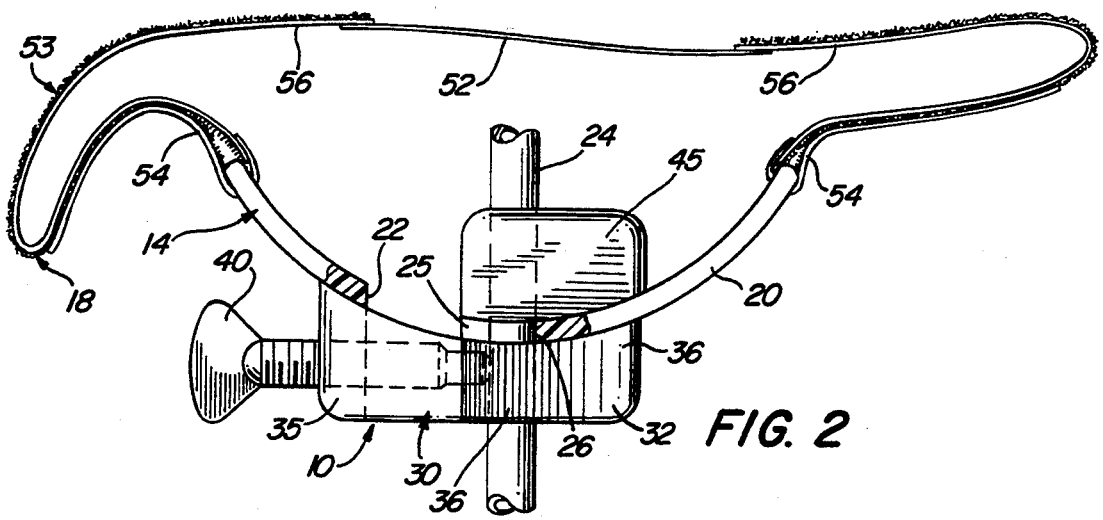
FIG. 2 is a top plan view of the present invention showing the relative position between the tube-holding block assembly and the rearwardly positioned bite block having an endotracheal tube mounted therein, with a portion of the face plate broken away.
Figure 3:
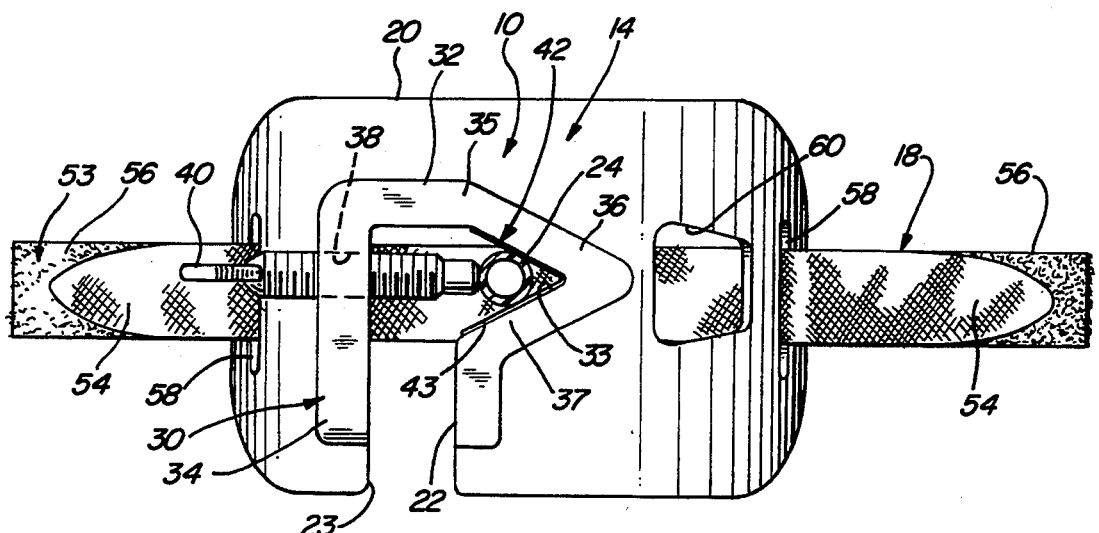
FIG. 3 is a front-elevational view thereof.
Figure 4:
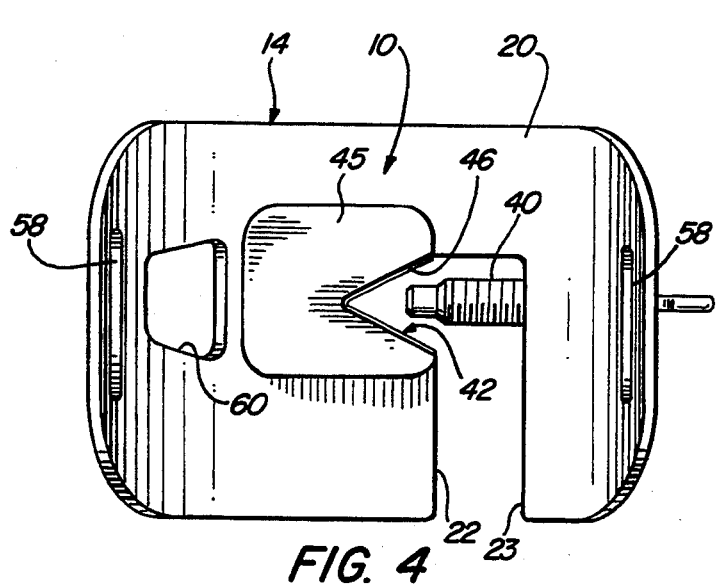
FIG. 4 is a rear-elevational view with the headband removed.

To provide a positive securing means for the endotracheal tube there is integrally mounted to the outer surface of face plate 20 a tube-holding block assembly, designated generally at 30, which comprises a holding-block member 32 and preferably made of polyethylene which is integrally molded into face plate 20, as shown in FIGS. 1, 2 and 3.

Holding-block member 32 is provided with a configuration that allows it to be superposed substantially over the perimeter of channel 22 of the face plate. Accordingly, the configuration of holding block member 32 comprises a vertical mounted wall 34, and an integral horizontal wall 35 which extends outwardly to establish a substantially V-shaped securing notch 33 which is defined by a pair of converging wall members 36 and 37 adapted to receive an endotracheal tube 24 of any suitable size, as illustrated in FIGS. 1, 2 and 3.

Vertical wall 34 of the member 32 includes a threaded bore 38 in which is threadably mounted a thumb screw 40, also preferably formed of polyethylene. An additional holding means, indicated at 42, comprising a dualsided adhesive tape 43 is secured to the inner surface of V-shaped notch 33 for engagement with tube 24 before thumb screw 40 is tightened against tube 24. The two-sided adhesive tape not only holds tube 24 in place while thumb screw 40 is tightened but also cooperates to prevent both longitudinal and rotational movement that may be inadvertently applied to the endotracheal tube once it has been correctly positioned in the patient's mouth and trachea.

There is also provided a bite block 45, having a substantially rectangular configuration, integrally mounted to the rear surface of face plate 20. Bite block 45 is made from a suitable firm but somewhat soft plastic material that is comfortably structured and adapted to be positioned within the patient's mouth so that it can be firmly grasped by the teeth without affecting the tube mounted therethrough.

A V-shaped notch 46, which is defined by a pair of converging inclined surfaces, is formed in one side of the bite block so that it aligns with both corresponding V-shaped notches 26 and 33 of the respective channel 22 and the tube-holding block assembly 30.

The adjustable attaching means 18, as heretofore mentioned, comprises a headband that is formed having an intermediate stretchable section defined by an elastic cloth strip 52 that has a limited stretch capability to prevent the patient from readily removing the headband. Each end of intermediate elastic strip 52 has an interlocking strip of material 53, such as VELCRO®. This interlocking strip 53 comprises a first section of hook material 54 and a second section of loop material 56 which are secured to each other.

Each oppositely disposed hook strip 54 is arranged to be inserted through slots 58 formed in face plate 20. Each hook section 54 is looped about its respective slot 58 so as to be adjustably connected to the corresponding loop strip 56.

Accordingly, both ends of the headband can be adjusted whereby the endotracheal tube-holder apparatus can be properly positioned over the patient's mouth, as illustrated in FIG. 1. If desire, the entire headband may be made of a stretchable material having a limited stretch capacity with suitable Velcro® sections at least one end thereof.

It should be noted that face plate 20 is provided with an access opening 60 which permits various medical instruments to be passed through so as to be inserted into the mouth of the patient, as may be necessary.

The foregoing should only be considered as illustrative of the principles of the invention. Further, since numerous modifications and changes may readily occur to those skilled in the art, it is not desired to limit the invention to the exact construction and operation as shown and described, and accordingly, all suitable modifications and equivalents may be resorted to, falling within the scope of the claimed invention.

What is claimed is:

1. An endotracheal tube holder having a face plate assembly so as to fixedly receive an endotracheal tube therein, said face plate assembly comprising:

an elongated face plate for placement over the mouth of a patient;

said face plate having a channel formed to include an open end to receive the endotracheal tube therethrough, and a closed end defined by a notch in which the endotracheal tube is fixedly positioned;

a tube holding block integrally mounted to the outer surface of said face plate, said tube holding block having a tube access opening and a tube holding notch for fixedly receiving said tube therein, whereby said tube holding block is superposed over said channel, said notch of said channel and said tube holding notch of said tube holding block being aligned with each other;

a bite block including a tube receiving notch formed therein, said bite block being integrally secured to the inner surface of said face plate;

a securing means operably mounted in said tube holding block for fixedly engaging said tube positioned in said tube holding notch; and means for adjustably mounting said face plate assembly for positioning said face plate over the mouth of the patient.

2. The invention as recited in claim 1, wherein each of said notches of said face plate, said tube holding block, and said bite block are formed having a substantially V-shaped configuration defined by a pair of converging flat surfaces.

3. The invention as recited in claim 2, wherein said securing means of said tube holding block comprises a thumb screw mounted to fixedly engage said tube positioned in said notch of said holding block.

4. The invention as recited in claim 3, wherein said face plate includes a pair of vertical slots disposed adjacent the opposite ends thereof, and wherein said adjustable mounting means comprises a headband having a pair of oppositely disposed securing strips that are mounted through the respective vertical slots of said face plate.

5. The invention as recited in claim 4, wherein said headband includes an elastic intermediate strip having the opposite terminating ends thereof attached to one end of each of said securing strips.

6. The invention as recited in claim 5, wherein said securing strips are formed with a first section of hook members and a second section of loop members, whereby said first and second sections are arranged to removably interlock with each other.

7. The invention as recited in claim 6, wherein said tube holding block is formed having a first vertical wall in which a threaded bore is disposed to threadably receive said thumb screw, and an oppositely disposed second vertical wall integrally connected by an intermediate horizontal wall, said second vertical wall being formed with a pair of converging members so as to define said V-shaped notch, and wherein said threaded bore in said first vertical wall is aligned with said V-shaped notch of said second wall.

8. The invention as recited in claim 3, including holding means comprising a dual-sided adhesive tape secured to the inner surface of said V-shaped notch of said tube holding block.

9. The invention as recited in claim 8, wherein said face plate includes an access opening positioned therein to allow free access to the patient's mouth, as may be required.

10. In combination, an endotracheal tube holder defining a face-plate assembly in which is fixedly received an endotracheal tube, the improvement comprising:

an elongated arcuate face plate for placement over the mouth of the patient, said face plate having a substantially L-shaped channel formed with a tube-access open end to receive the endotracheal tube therethrough, and a closed end defined by a V-shaped notch in which the endotracheal tube is fixedly positioned;

a tube holding block integrally mounted to the outer surface of said face plate, said tube holding block having a tube access opening and a tube holding V-shaped notch for fixedly receiving said tube therein, wherein said tube holding block is superposed over said channel so that said V-shaped notch of said channel and said V-shaped notch of said tube holding block are aligned with each other;

a bite block having a V-shaped notch formed therein, said bite block being integrally secured to the inner surface of said face plate;

a securing means operably mounted in said tube holding block for fixedly engaging said tube positioned in said V-shaped notch of said tube holding block; and an adjustable headband mounted to said face plate for positioning said face plate assembly on the face of the patient.

11. The combination as recited in claim 10, wherein said securing means of said tube holding block comprises a thumb screw operably mounted to fixedly engage said endotracheal tube within said V-shaped notch of said holding block.

12. The combination as recited in claim 11, wherein said face plate includes a pair of vertical slots located adjacent the opposite ends thereof, and wherein said headband is formed having a pair of oppositely disposed securing strips that are mounted through the respective vertical slots of said face plate.

13. The combination as recited in claim 12, wherein said headband includes an intermediate longitudinal stretchable elastic strip having opposite terminating ends which are respectively attached to one end of each securing strip.

14. The invention as recited in claim 13, wherein said securing strips are formed with a first section of hook members and a second section of loop members, whereby said first and second sections are arranged to removably interlock with each other.

15. The combination as recited in claim 14, wherein said tube holding block is formed with a first vertical wall in which a threaded bore is disposed to threadably receive said thumb screw therein, and an oppositely disposed second vertical wall integrally connected by an intermediate horizontal wall, said second vertical wall being formed with a pair of converging members so as to define said V-shaped notch, wherein said threaded bore in said first vertical wall is aligned with said V-shaped notch of the opposite second wall.

16. The combination as recited in claim 10, including holding means comprising a dual-sided adhesive tape secured to the inner surface of said V-shaped notch of said tube holding block.

17. An endotracheal tube holder assembly comprising:

a face plate formed to be positioned over the mouth of a patient;

a tube receiving channel formed in said face plate, said channel being defined by an open end to receive an endotracheal tube, and a closed notched end in which said endotracheal tube is positioned;

a tube holding block integrally mounted to the outer surface of said face plate, wherein said tube holding block is formed with a tube receiving opening and a notch superposed over said closed notched end of said channel;

a securing means operably mounted in said tube holding block for fixedly securing said endotracheal tube in said notch of said tube holding block;

a bite block integrally mounted to the rear surface of said face plate, said bite block being formed with a notch corresponding to said notch of said channel and said tube holding block; and means for adjustably attaching said endotracheal tube holder assembly to the head of the patient, said means being adjustably coupled to the opposite ends of said face plate.

18. An endotracheal tube holder assembly as recited in claim 17, wherein said face plate is formed with an elongated arcuate configuration to fit the contour of the patient's mouth, wherein said face plate includes an access opening which permits various medical instruments to be passed through so as to be inserted into the mouth of the patient as may be necessary, and wherein a pair of slots are formed adjacent the opposite end of said face plate to which said attaching means is adjustably coupled.

19. An endotracheal tube holder assembly as recited in claim 17, including a tube holding means mounted in said notch of said tube holding block, whereby longitudinal and rotational movement of said endotracheal tube is prevented.

20. An endotracheal tube holder assembly as recited in claim 19, wherein said tube holding means is defined by a dual-sided adhesive strip mounted to the surface of said notch of said tube holding block.

21. An endotracheal tube holder assembly as recited in claim 17, wherein said securing means comprises a thumb screw threadably mounted in said tube holding block and positioned so as to forcibly engage said endotracheal tube in said notch of said tube holding block.

22. An endotracheal tube holder assembly as recited in claim 21, including a tube holding means mounted in said notch of said tube holding block, whereby longitudinal and rotational movement of said endotracheal tube is prevented.

23. An endotracheal tube holder assembly as recited in claim 22, wherein said tube holding means is defined by a two-sided adhesive strip, one side which being mounted to the surface of said notch of said tube holding block and the opposite adhesive side being positioned to engage said endotracheal tube.

24. An endotracheal tube holder assembly as recited in claim 21, wherein said notch of said tube holding block is formed having a V-shaped configuration defined by a pair of merging inclined walls and an oppositely disposed wall having a threaded bore formed therein to threadably receive said thumb screw.

25. An endotracheal tube holder assembly as recited in claim 21, wherein said means for adjustably attaching said endotracheal tube holder assembly to the head of the patient comprises a headband formed with an intermediate stretchable member defined by an elastic cloth strip and a pair of interlocking strips, each of said strips having a hook section and a loop section, wherein said interlocking strips are attached to the respective opposite ends of said intermediate stretchable member and positioned in said respective slots of said face plate.

* * * * *